United States Patent [19]

Touboul et al.

[11] Patent Number: 5,181,513
[45] Date of Patent: Jan. 26, 1993

[54] METHOD OF ACQUIRING ULTRASOUND IMAGES

[75] Inventors: Pierre-Jean Touboul, 20 rue de Berri, 75008 Paris; Siv-Cheng Tan, Saint Maur, both of France

[73] Assignees: Pierre-Jean Touboul, Paris; Traitement Synthese Image, Meudon la Foret, both of France

[21] Appl. No.: 704,800

[22] Filed: May 23, 1991

[30] Foreign Application Priority Data

May 29, 1990 [FR] France .................... 90 06633

[51] Int. Cl.$^5$ .............................................. A61B 8/08
[52] U.S. Cl. .................................................. 128/660.07
[58] Field of Search ...................... 128/660.01, 660.06, 128/660.07, 660.04–660.05, 661.07–661.10

[56] References Cited

U.S. PATENT DOCUMENTS

| | | | |
|---|---|---|---|
| 4,263,916 | 4/1981 | Brooks et al. | 128/654 |
| 4,431,007 | 2/1984 | Amazeen et al. | 128/660.04 |
| 4,448,200 | 5/1984 | Brooks et al. | 128/660.01 X |
| 4,922,909 | 5/1990 | Little et al. | 128/774 X |
| 5,056,524 | 10/1991 | Oe | 128/654 |

*Primary Examiner*—Francis Jaworski
*Attorney, Agent, or Firm*—Bachman & LaPointe

[57] ABSTRACT

Ultrasound images are rendered reproducible over long time periods by determining contours of a first image and superimposing them on a real time display screen during acquisition of a second image. The operator manipulates the probe so that the new image fits within the contours obtained from the first image. This avoids the need for signal processing requiring powerful computer resources. It also avoids the use of complicated ultrasound images. The method may be implemented in any ultrasound equipment currently available on the market.

7 Claims, 2 Drawing Sheets

METHOD OF ACQUIRING ULTRASOUND IMAGES

BACKGROUND OF THE INVENTION

1. Field of the Invention

The present invention concerns a method of acquiring ultrasound images, in particular in medical applications. The object of the invention is to enable ultrasound images obtained at different times in the life of a patient to be compared to determine whether pathological conditions indicated by a first image have developed with time.

2. Description of the Prior Art

The general principle of acquiring ultrasound images is familiar. It uses ultrasound equipment comprising a probe incorporating piezo-electric transducers. The equipment also includes control circuitry connected to the transducers which emit and receive ultrasound waves. To obtain an image of a part of the body of a patient the probe is placed against the skin of the patient near the part concerned. The ultrasound waves emitted by the probe are reflected by the tissues of the part of the body being examined and are received by the probe. This converts the ultrasound waves into electrical signals which are then processed. The main purpose of this signal processing is to produce an image of a cross-section of the body in the area concerned (a tomograph).

The cross-section to be imaged is scanned by the ultrasound waves. Two-dimensional scanning of the cross-section plane by the ultrasound waves is obtained for a given direction of emission by establishing the relationship between the signals received and the time at which they are received. Given the propagation speed of ultrasound waves in human tissue (which is in the order of 1,500 meters per second, given the high water content of human tissue), the signals reflected from deeper areas of the body reach the probe later. The signals from deeper parts of the body are usually attenuated. This attenuation can be compensated by applying amplification with a gain that varies with time.

To scan in the other direction the direction of emission is changed. There are various scanning modes. In lateral scanning the direction of emission is moved parallel to itself. In angular scanning the emission directions cover a portion of a circle (a fan shape).

The images produced by a probe can be displayed on a visual display unit in real time by electronically scanning the emission direction in synchronism or in some other corresponding relationship with the vertical scanning of the monitor. To this end the monitor video signal is conditioned by the amplitude of the detected, demodulated and filtered ultrasound signal.

Ultrasound equipment usually incorporates means for storing images. Rather than using an analog representation of the received ultrasound signals, the signals are digitized and stored in digital form. It is then possible, using an image memory and a display monitor, to display digitized images rather than the analog images themselves. Modern equipment uses methods of digitizing the analog signals produced by the probe so quickly that even with a digital image store real time display is possible. The display monitor shows the image contained in the image store. This is continually updated with new images produced by further scans.

The images produced enable a practitioner to detect the presence of particular pathologies. In the vessels of the neck, for example, the practitioner is looking for lesions or the appearance of atheroma plaques whose brightness in the image depends on how far advanced is the process of lipid-fibrosis-calcification. This is because their density increases their reflection coefficient. By reducing the flexibility of the blood vessels, the atheroma plaques slow the flow of blood and can eventually cause lesions to the brain through inadequate blood supply. It is therefore important to monitor this development. An image is therefore obtained of a region likely to contain or already containing such atheroma plaques. Later, for example a few months later, an equivalent image is obtained of the same part of the body. The two images are then compared in order to evaluate the degree to which the pathology in question has developed.

This comparison is difficult. It is affected by variations in image acquisition conditions. One attempt to solve this problem was described in 1983 in Radiology volume 148, no 2, pages 533–537 by David H. BLAND-ENHORN et al, in an article entitled "Common carotid artery contours reconstructed in three dimensions from parallel ultrasonic images". In the technique described, the probe is fastened to a motor-driven boom which is adapted to move the probe forward by calibrated amounts in order to obtain parallel sections. This produces a three-dimensional reconstruction of the relevant part of the patient's body. A similar process could be conducted on the same patient six months later. The 3D reconstructions could then be examined for corresponding tomographs in order to evaluate any development that may have taken place. Apart from the complexity of the equipment used, in particular to achieve calibrated movement of the probe, this technique could not yield conclusive results as the images depend on the power emitted each time. The images must therefore be calibrated. The theory of acoustical absorption by tissue does not provide any means of normalizing the power output of the emitters. The experiment is adversely affected by drift in the power output of the equipment. The brilliance is influenced by the power output. Also, the non-linear nature of the absorption phenomena means that normalization is not possible.

In another publication, "Evaluation of a scoring system for extracranial carotid atherosclerosis extent with B-mode ultrasound" by John R. CROUSE et al published in STROKE—volume 17 no 2 March-April 1986, pages 270 through 275, measurements of the severity, in other words the thickness of the largest atheroma plaque detected in a patient were carried out at different times for a sample of patients. This study concluded that the correlation between the first and second sets of measurements was low, given that attention was focused on the most severe lesion. However, there was better correlation between so-called "extension" measurements, relating to the sum of the axial thicknesses of all the local obstructions. Although the conclusions of this publication provide useful statistical elements, their teaching in response of individual patients is simply stated: the difficulty of comparing images acquired at one tim with images acquired at another time means that evaluating the development of a pathology is doubtful.

X-ray angiography and other techniques use image recalibration techniques in which one of two images is processed and then subtracted from the other. Distortion is corrected before the image is superimposed on the other image. This technique requires powerful computer systems (it uses very large amounts of memory) and cannot be transported to the ultrasound domain because the orientation of the ultrasound probe relative to the body of the patient is not maintained as accurately as is the orientation of an X-ray tube relative to the body of the patient in an X-ray angiography application.

The object of the invention is to remove these drawbacks by proposing an entirely different method which is directly accessible to all practitioners using existing ultrasound equipment. The invention produces not only statistical results that can be applied to a population of patients, but also results relating to each individual patient. The invention, differing in this respect from prior art practise, is based on the observation that practitioners themselves, with some experience, can perceive in real time the structures that they wish to demonstrate. It is considered, for example, that after carrying out ultrasound examinations of some 300 to 400 different patients, the practitioner acquires considerable skill in manipulating the probe in such a way as to show on the display what he wishes to see, in particular to acquire a first image, the lesions and the atheroma plaques in the carotid arteries of the neck.

Rather than apply distortion correcting processing to images acquired subsequently by these practitioners, the idea is to impose an additional constraint on practitioners with regard to acquiring the second images. This additional constraint requires them to place the probe in exactly the same position to obtain the second image as when the previous image was acquired. To embody this constraint in concrete terms, there is produced as a background to the real time display screen the contours of the tissues examined when the first image was acquired.

This requires the practitioner to display an image representing the lesion and to refine the representation of the lesion by manipulating the probe (by moving his hand) so that the second image is rendered as accurately coincident as possible with the background image. This process might be described as placing the second image in the first image. The background image may be highlighted (displayed with increased brightness). Practical experience by the inventors has shown that around 50 additional examinations are sufficient to obtain sufficient skill for a second image to be regarded as having been acquired with substantially the same conditions of probe inclination and incidence angle as the first image.

To solve the problem of power variation, part of the displayed image includes information on tissue density. This information is obtained by measuring the average brightness of the picture elements (pixels) contained in a geometrical figure (a circle) in the first image and the same figure at the same place in the new image. By adjusting a gain control, the practitioner operating the equipment can then adjust the power and/or the waveform of the ultrasound pulses until the measurements are compatible. When this has been done, the change in the brightness of the atheroma plaques can be determined to deduce whether or not it has become more calcified since the last examination.

This visual validation is regarded as subjective in the sense that it requires human evaluation of the measured resemblance. It is related to the discernment of the practitioner and is not the result of objective processing applied by a machine using an automatic process. Nevertheless, this subjective visual validation has advantages over previous practise. In particular, the second image can be acquired by a different practitioner from the practitioner who obtained the first image. Also, the fact that a contour from the first image is shown produces better results than would be obtained by attempting to present all of the first image.

In some known systems the display screen is divided into two parts in real time, the lefthand part, for example, showing the first image and the righthand part showing the new image being acquired. In such cases, given the existence of a lesion or other pathology in the first image, the practitioner works instinctively towards a second image in which the lesion appears larger, the same size or smaller, depending on whether the practitioner is unconsciously motivated to show an aggravation, a stagnation or a regression of the pathology. In this case the subjective element is too strong and the measurements are unreliable.

However, by showing only the contour of the first image, and optionally the density information, the practitioner is obliged to acquire an image which agrees as closely as possible with the older image without knowing what is expected on subsequently comparing the second image with the complete first image (and not just its contours). It is only then that the pathological areas in the new image are compared with the first image. The approach is different in the sense that the importance of the previously measured pathology is not revealed to the practitioner in real time, but later as an objective result of comparison. In effect, as the pathology is not present in the contour image displayed, it cannot influence the practitioner.

The invention therefore secures morphological and densitometric reproducibility of images based on the mental integration aptitudes of the practitioner manipulating the probe. This additional aptitude is obtained at the cost of only some 50 experiments, as has been established. The required dexterity is then obtained. Experience shows that the practitioner chooses the contours in the first image more and more quickly with practise: this means even with a small number of points. It has been found that reproducibility is not total, however. On the other hand, it is clearly better than what has been achieved previously. For example, it has been possible to perceive growth of lesions in the order of 5%, which was not possible with earlier techniques.

In one embodiment of the invention, the fact that modern ultrasound equipment incorporates an image store and means for storing digitized images is exploited. As the practitioner manipulates the probe, in the proximity of the final orientation and inclination that is required, the various images obtained are stored in real time. Subsequently, off-line, the best image can be chosen from the series of images, by which is meant the image that fits best by superposing the contours shown on the screen and relating to the first image.

It has been found that this technique is of particular benefit when studying cyclic phenomena. It is therefore particularly interesting in studying the phenomenon of blood flow in the arteries, in itself another limitation of older techniques.

SUMMARY OF THE INVENTION

The invention consists in a method of acquiring medical ultrasound images using ultrasound equipment provided with a probe and a screen for displaying images produced in real time, in which method:

the equipment is used to acquire a first image of a region of the body of a patient to be examined, with a particular angle of incidence and inclination of said probe, a practitioner subsequently acquires a second image of the same region of the body of the same patient with the same angle of incidence and inclination of the probe of the same equipment.

the two images acquired are compared to evaluate changes in the body of the patient between the date of the first image and that of the second image, the practitioner is assisted to obtain the second image by producing on the display screen in real time an image of contours of structures from the first image, and the practitioner manipulates the probe so that the structures of the second image, visible in real time, are superimposed on the contour image already present in the first image.

The invention will be better understood from the following description given by way of non-limiting example only with reference to the appended drawings.

DETAILED DESCRIPTION OF THE INVENTION

Figure 1:
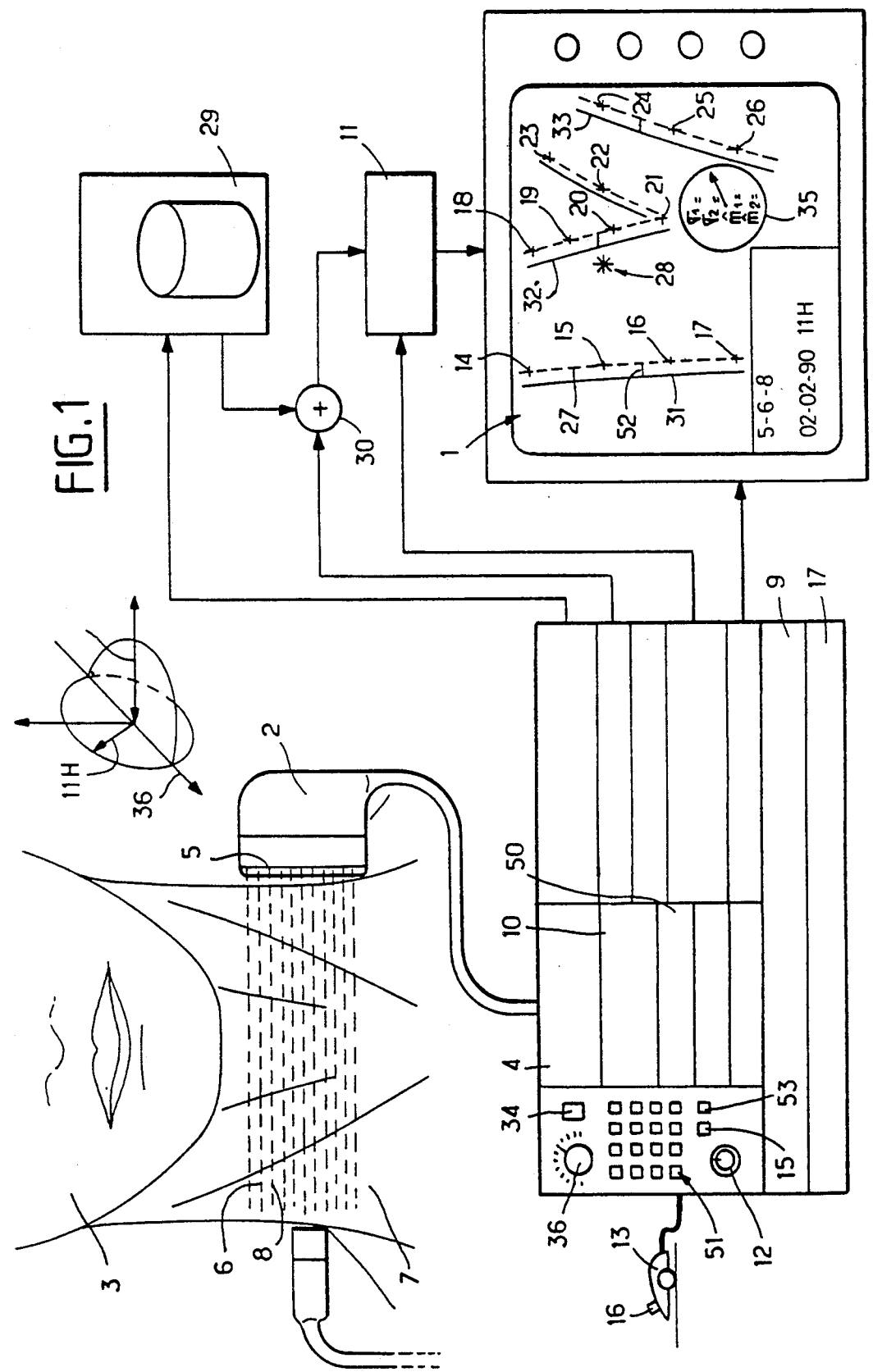
FIG. 1 is a diagram showing ultrasound equipment for implementing the method in accordance with the invention.

FIG. 1 shows ultrasound equipment for implementing the method in accordance with the invention. The equipment includes a display screen 1 for real time display of the images produced. Images are acquired at two different dates. Apart from the aspects relating to the present invention, the known acquisition process is the same in both cases. It involves placing an ultrasound probe 2 against a region of the body of a patient 3. In this example the region to be examined is the neck and the application described is in the field of arteriography. It is feasible to use the invention for other purposes, in particular to examine the vascular tree of the lower or upper members or of organs situated in the trunk: the stomach, the liver.

The ultrasound equipment conventionally comprises transceiver means 4 for sending electric signals to the probe 2 and receiving electric signals from the probe. In the probe the input electrical signals are converted into ultrasound waves by piezo-electric transducers 5. These electrical signals are, for example, short pulses with a high repetition frequency (in the order of 10 MHz) fed by known methods to the various transducers 5 so as to focus the emission in the emission direction 6. As soon as the excitation pulse ends a multiplexer switches the equipment to receive mode. The piezo-electric transducers 5 convert into electrical signals the ultrasound waves reflected from the neck 7 of the patient. The reflected ultrasound waves reach the transducers 5 at progressively later times according to the distance between the probe 2 and the area from which they are reflected. When all the signals for a given direction have been received, ultrasound waves are emitted in a nearby direction (the direction 8, for example) and the reflected levels are measured.

The scanning of the emission directions 6 and 8 and the reception of the ultrasound signals are controlled by a microprocessor 9. This manages the row and column scanning of the display monitor 1. If fan-mode scanning of the emission direction is used rather than lateral scanning, the display on the monitor 1 is organized accordingly.

The measures signals are demodulated and filtered in an operation 10. As previously mentioned, rather than using a filtered demodulated analog signal as the video signal the trend is increasingly towards digitizing the analog signal in an operation 60. The digital signal is then passed to an image memory 11 which is also read under the control of the microprocessor 9. The microprocessor reads data at each cell address of a memory page of the image memory and uses this data as a luminance and/or chrominance signal to control the brightness of a pixel on the monitor 1.

The prior art provides systems for pointing to particular locations on the images. A practitioner uses a trackball 12 or a mouse 13 to move a cursor, for example a cruciform cursor 14, to any particular place on the screen. The location is memorized by pressing a button 15 on the track-ball or 16 on the mouse. The microprocessor 9 then stores in its working memory 17 the coordinates of the screen location of the cursor 14. It relates the coordinates of this location to an address in a memory page of the image memory. The practitioner can then move the cursor to another position 15. The positions 14 and 15 are located on a contour of the first image. The addresses of the cursor positions 14 through 26 can then be stored.

A known technique for displaying a straight line segment joining two points on the screen can be used to store in the memory 17 and to show in superimposition on the screen 1 the segment 27 between the points 14 and 15. Spline type techniques are used to draw a second degree curve (rather than a straight line) through a number of predetermined points: for example the points 14 through 17, or 18 through 21, or 21 through 23, or 24 through 26. The start and end of the curve segment are designated using the keyboard 51 of the ultrasound equipment.

In the context of the invention, and given the acquisition of a first image showing an atheroma plaque 28, a special cursor (asterisk-shape in this example) can be used to point to the plaque to indicate the presence of a lesion. This enables the practitioner to verify subsequently that the same lesion exists in the new images. When the contours 14 through 26 and the segments 27, etc. have been generated, rather than remaining in the memory 17 the segments are loaded into a contour image contained in a stored image memory 29. This contour acquisition process is preferably executed on a first display image shown on the screen 1.

When the second image is acquired, images acquired in real time are sent direct to the monitor 1 via the image memory 11. The image memory contains for each pixel address on the screen 1 a brightness indication representing the digitized value of the ultrasound signal detected in real time. An adder 30 is then used to add pixel by pixel (using the proper addresses) the luminous information relating to the contours of the first image previously stored in the stored image memory 29. In other words, during the second acquisition the practitioner sees on the screen the contours 14 through 27 and the asterisk 28. He must then manipulate the probe 2 until the image produced on the screen in real time, symbolically represented here by the continuous lines 31 through 33, is superimposed exactly on the contours shown by the crosses and the dashed lines. In a favorable case this might be limited to moving the real time image as shown by the arrow 52.

Some 50 experiments are required to achieve this degree of skill. When the practitioner considers that registration has almost been achieved he can press a button 34 to store in the memory 17 the successive images produced by the probe 2 and representing successive scans. If the practitioner is highly experienced he will be able to obtain stable registration very quickly. A less experienced practitioner will require rather more trial and error. In both cases, by storing a series of images it is possible to examine the plurality of images acquired during the second acquisition process in order to choose the one which achieves the best registration.

To overcome the problem of gain, the first image includes a pattern (for example a circle 35) for which it is possible to determine for all pixels that it contains the value m and the mean standard deviation $\sigma$ of the brightness variation. The pattern 35 is preferably located in a relatively stable part of the image, where the reflected and recovered signal varies little however much the orientation of the probe is altered. To obtain the average it suffices to add all the information values contained in the memory cells contained in the image memory 11 and representing the interior of the pattern 35, and to divide the result of this addition by the number of pixels. The mean standard deviation is calculated in a similar way. Just as the stored image comprises the position of the points 15 through 26 and the position of the segments 27, etc., the position of the pattern 35 and the values $\sigma_1$ and $m_1$ of the first image can be stored.

During acquisition of the second image it is possible to show each time below the corresponding value the values $\sigma_2$ and $m_2$ for the brightness of the pixels located in the same pattern 35 at the same location. These simple calculations can be carried out by operators receiving continuous brightness information from the memory cells concerned. The practitioner can then alter the gain of the ultrasound equipment by turning a gain knob 36 to vary the power of the ultrasound signals emitted by the probe 5. In this way the brightness values can be equalized for the first and second images. They must be the same or as close as possible. The brightness values in fact represent the density of the material encountered. The denser the material, the more signals will be reflected and the higher will be the average value m. The circle 35 is preferably placed at a location where the average is low.

To provide further assistance to the practitioner identifying information is overlaid on the screen display, showing the name of the patient, the date of the first acquisition, the orientation (11H) and the angle of incidence (RIGHT LATERAL) of the probe when the first image was acquired. The orientation is an orientation relative to the vertical and identifies the position of the probe in the vertical plane using the standard clock face notation (i.e. 11 o'clock, in this example). The angle of incidence shows, relative to an axis 33 passing through the back of the patient, the anterior, posterior, lateral or intermediary orientation of the probe. It is also possible to indicate segments 5-6-8 of carotid arteries displayed.

Figure 2:
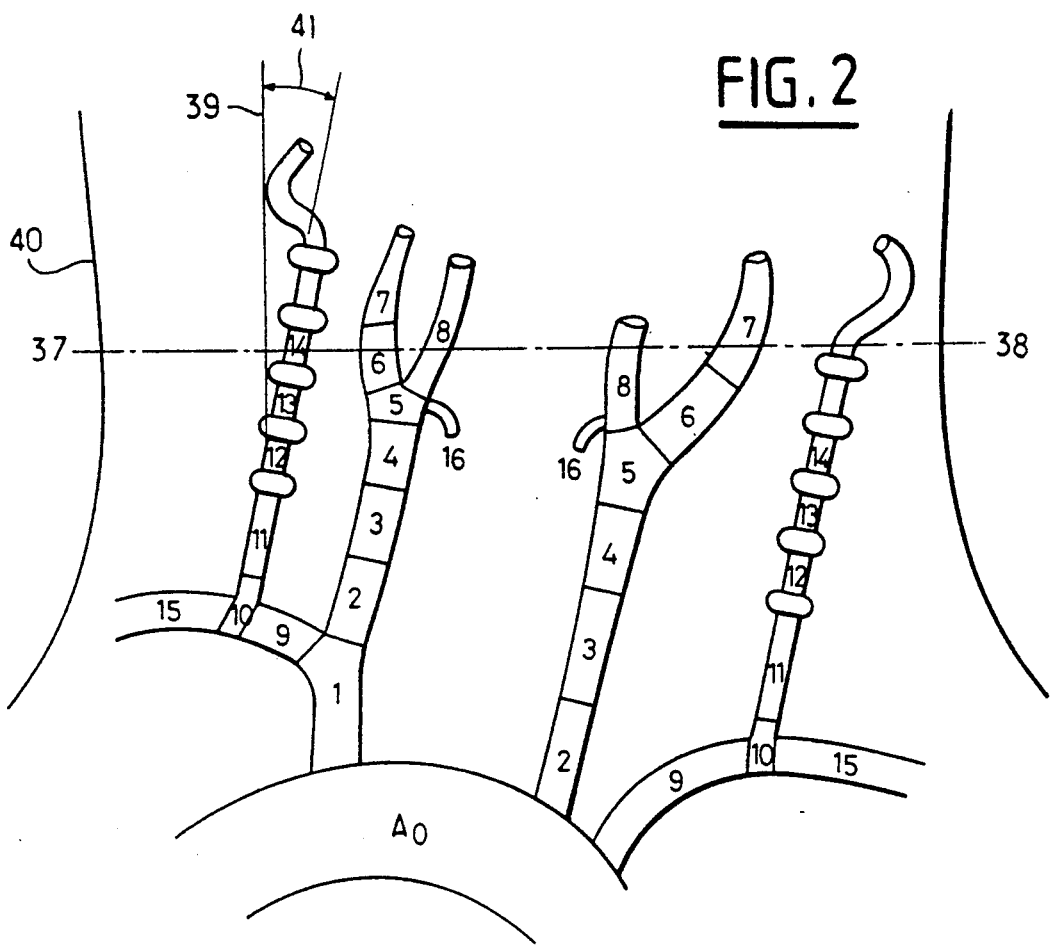
FIG. 2 is a schematic representation of the neck of a patient.

FIG. 2 is a schematic representation of the anatomy of the carotid artery segments.

The numbered segments are:
1 brachiocephalic artery,
2 lower common carotid artery,
3 middle common carotid artery,
4 upper common carotid artery,
5 carotid artery bifurcation,
6 carotid sinus,
7 sub-sinusoidal internal carotid artery,
8 external carotid artery,
9 pre-vertebral sub-clavian artery,
10 sub-clavian artery and beginning of vertebral artery,
11 pre-transversal vertebral artery,
12 first segment of inter-transversal vertebral artery,
13 second segment of inter-transversal vertebral artery,
14 third segment of inter-transversal vertebral artery,
15 post-vertebral sub-clavian artery.

When the second image is acquired this information tells the practitioner where and approximately how to place the probe. This information is broadly sufficient for the distance 52 through which the real time image must be moved to achieve superimposition not to be greater than the size of the screen.

Figure 3:
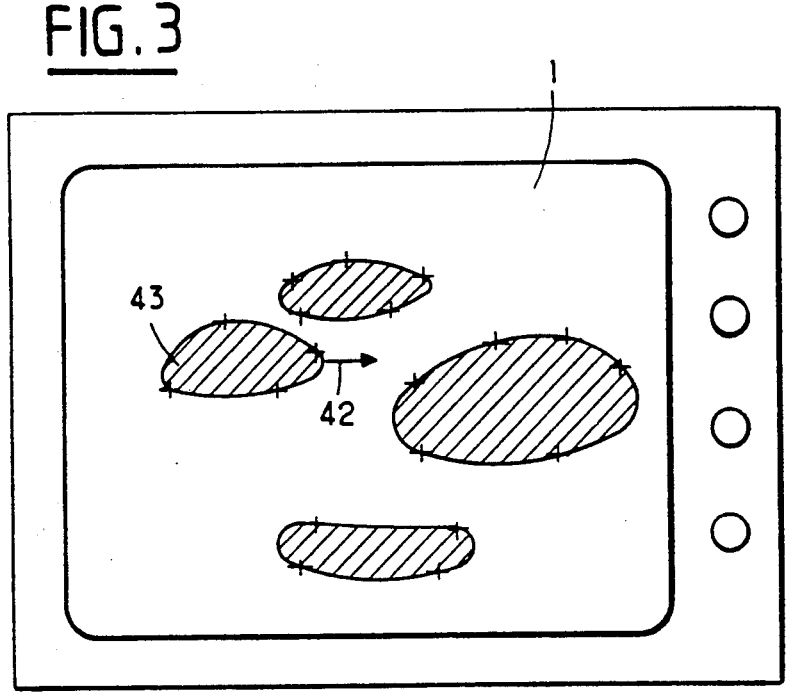
FIG. 3 is an image obtained from the neck shown in FIG. 2 with a transverse inclination of the ultrasound probe.

FIG. 3 shows the contour image obtained from a first acquisition of a transverse cross-section on the line 37-38 in FIG. 2. It might seen that the contours shown are insufficient to show the height at which the first image was obtained. It has been found, however, that this problem does not arise because the vessels concerned do not have the same diameter along their length and because they are not oriented vertically. All the vessels are at a particular angle, such as the angle 41, to the vertical 39 (parallel to the edge 40 of the neck) along which the probe 2 moves. On moving vertically upwards, the angle 41 results in a displacement of the images of the structure concerned in the direction of the arrow 42. In other words, given an acquired and displayed image 1 it is possible to obtain a representation of the second image relatively quickly. In this case it is beneficial for the cross-sections to have slightly more segments or contours that non-transverse cross-section images. The latter require on average a dozen points whereas approximately twice this number of points are required for transverse cross-section images.

Of course, the invention is not limited to the embodiment described above and variations thereon may be put forward without departing from the scope of the invention.

There is claimed:

1. Method of acquiring medical ultrasound images using ultrasound equipment provided with a probe and a screen for displaying images produced in real time comprising the steps of:
   a) acquiring at a first date with said equipment during a first examination of a patient a first image of a region of the body of said patient to be examined with a particular angle of incidence and inclination of said probe, said first image comprising contours of vascular structures; and
   b) acquiring at a second subsequent date with said equipment during a second further examination of said patient a second image of said region of the body of said patient by the following steps:
      1) producing on the display screen an image of contours of vascular structures from the first image;
      2) manipulating said probe until vascular structures of the image of said region of the body, visible in real time on said display screen, are superimposed on the displayed contours of vascular structures from the first image; and 3) acquiring as said second image said displayed image when said superimposition is obtained, whereby the second image has substantially the same angle of incidence and inclination of the probe as the first image.

2. A method according to claim 1 including the step of comparing said second image to said first image to determine changes in said region of the body of the patient from said first date to said second subsequent date.

3. A method according to claim 1 comprising displaying on said display screen in real time (1) information on the density of the tissue of the body relating to the first image and (2) information on the density of the same tissue of the body relating to the second image and, thereafter, (3) adjusting the ultrasound equipment so that the density information for each image is compatible.

4. A method according to claim 1 comprising displaying on the display screen in real time information relating to at least one of the following characteristics of the first image: (1) angle of incidence of the first image; (2) inclination of the first image; (3) patient's name; and (4) date the first image was acquired.

5. A method according to claim 1 comprising producing a contour image from the first image by the following steps: (1) storing and displaying said first image off-line on said display screen; (2) placing indexing points on said stored first image displayed on said screen; and (3) drawing curve through said indexing points on the screen.

6. A method according to claim 5 comprising producing a plurality of successive first images and selecting therefrom a desired first image from which the contour image is produced.

7. A method according to claim 1 comprising obtaining a valid second image by the following steps: (1) producing in real time a plurality of successive second images when the probe is substantially in the position used to acquire the first image wherein the second images are produced at the scanning rate of the ultrasound equipment; (2) storing said successive second images; and (3) selecting from said stored successive second images the single second image most closely resembling the first image.

* * * * *